US008841924B2

(12) United States Patent
Reccius et al.

(10) Patent No.: US 8,841,924 B2
(45) Date of Patent: Sep. 23, 2014

(54) FINGERED ELECTRODES FOR MICROFLUIDIC SINGLE PARTICLE ANALYSIS

(75) Inventors: Hermann Christian Reccius, Eindhoven (NL); Steven Charles Deane, Eindhoven (NL); Cees Van Berkel, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 282 days.

(21) Appl. No.: 13/146,244

(22) PCT Filed: Jan. 27, 2010

(86) PCT No.: PCT/IB2010/050355
§ 371 (c)(1),
(2), (4) Date: Jul. 26, 2011

(87) PCT Pub. No.: WO2010/086797
PCT Pub. Date: Aug. 5, 2010

(65) Prior Publication Data
US 2011/0279130 A1 Nov. 17, 2011

(30) Foreign Application Priority Data
Jan. 27, 2009 (EP) ..................... 09151418

(51) Int. Cl.
*G01N 27/00* (2006.01)
*G01R 27/08* (2006.01)
*C12Q 1/68* (2006.01)
*G01N 15/10* (2006.01)
*G01N 15/12* (2006.01)
*G01P 15/125* (2006.01)
*G01R 27/26* (2006.01)

(52) U.S. Cl.
CPC ........ *G01N 15/1227* (2013.01); *G01N 15/1056* (2013.01); *G01P 15/125* (2013.01); *G01N 2015/1254* (2013.01); *G01R 27/2605* (2013.01)
USPC .......... 324/649; 324/71.1; 324/693; 435/6.18

(58) Field of Classification Search
CPC .......... G01N 15/1227; G01N 15/1056; G01N 2015/1254; G01R 27/2605; G01P 15/125
USPC ................. 324/649, 692, 71.1, 693; 435/6.18
See application file for complete search history.

(56) References Cited

U.S. PATENT DOCUMENTS 5,132,824 A * 7/1992 Patel et al. ........................ 349/1
6,377,057 B1 * 4/2002 Borkholder ................... 324/692

(Continued)

OTHER PUBLICATIONS

Cheung, Karen et al "Impedance Spectroscopy Flow Cytometry: On-Chip Label-Free Cell Differentiation" Cytometry Part A, 65A, pp. 124-132, 2005.

(Continued)

*Primary Examiner* — Melissa Koval
*Assistant Examiner* — Farhana Hoque

(57) ABSTRACT

The electrical properties of particle solutions can be investigated on a single particle basis by using micro fluidic channels. The impedance can be measured across the channel using at least one pair of conductive electrodes, at least one electrode of a pair being a fingered electrode having a plurality of fingers. The pattern of fingered electrodes creates a longer and more complicated measurement signal shape which leads to a significant improvement of measurement sensitivity. An application for the proposed technology is to significantly improve the measurement sensitivity of impedance measurements on blood cells, leading to a better differentiation between different types of white blood cells. Better measurement sensitivity also enables the measurement of smaller particles and higher throughput.

14 Claims, 9 Drawing Sheets

(56) References Cited

U.S. PATENT DOCUMENTS

| | | | |
|---|---|---|---|
| 8,358,177 B2* | 1/2013 | Yamanaka | 331/154 |
| 2003/0203384 A1* | 10/2003 | Chafin et al. | 435/6 |
| 2007/0247173 A1* | 10/2007 | Tai et al. | 324/692 |
| 2008/0024111 A1* | 1/2008 | Dorfmueller et al. | 324/71.4 |
| 2009/0011430 A1* | 1/2009 | Ateya et al. | 435/7.2 |

OTHER PUBLICATIONS

Iliescu, Ciprian et al "Novel Microfluidic Device for Cell Characterization by Impedance Spectroscopy" Proc. of SPIE, vol. 6416, 2006, pp. F1-F6.

Gawad, Shady et al "Impedance Spectroscopy using Maximum Length Sequences: Application to Single Cell Analysis" Review of Scientific Instruments, vol. 78, pp. 54301-1-054301-7, 2007.

Madhukar, V. et al "Double Interdigitated Array Microelectrode-Based Impedance Biosensor for Detection of Viable *Escherichia coil* 0157:H7 in Growth Medium" Sciencedirect, Talanta, vol. 74, 2008, pp. 518-525.

Romanuik, S.F. et al "All Electronic Detection and Actuation of Single Biological Cells for Lab-on-a-Chip Applications" IEEE Sensors, 2008, pp. 634-637.

Zou, Zhiwei, A Polymer Microfluidic Chip with Interdigitated Electrodes Arrays for Simultaneous Dielectrophoretic Manipulation and Impedimetric Detection of Microparticles IEEE Sensors Journal, vol. 8, No. 5, May 2008, pp. 527-535.

\* cited by examiner

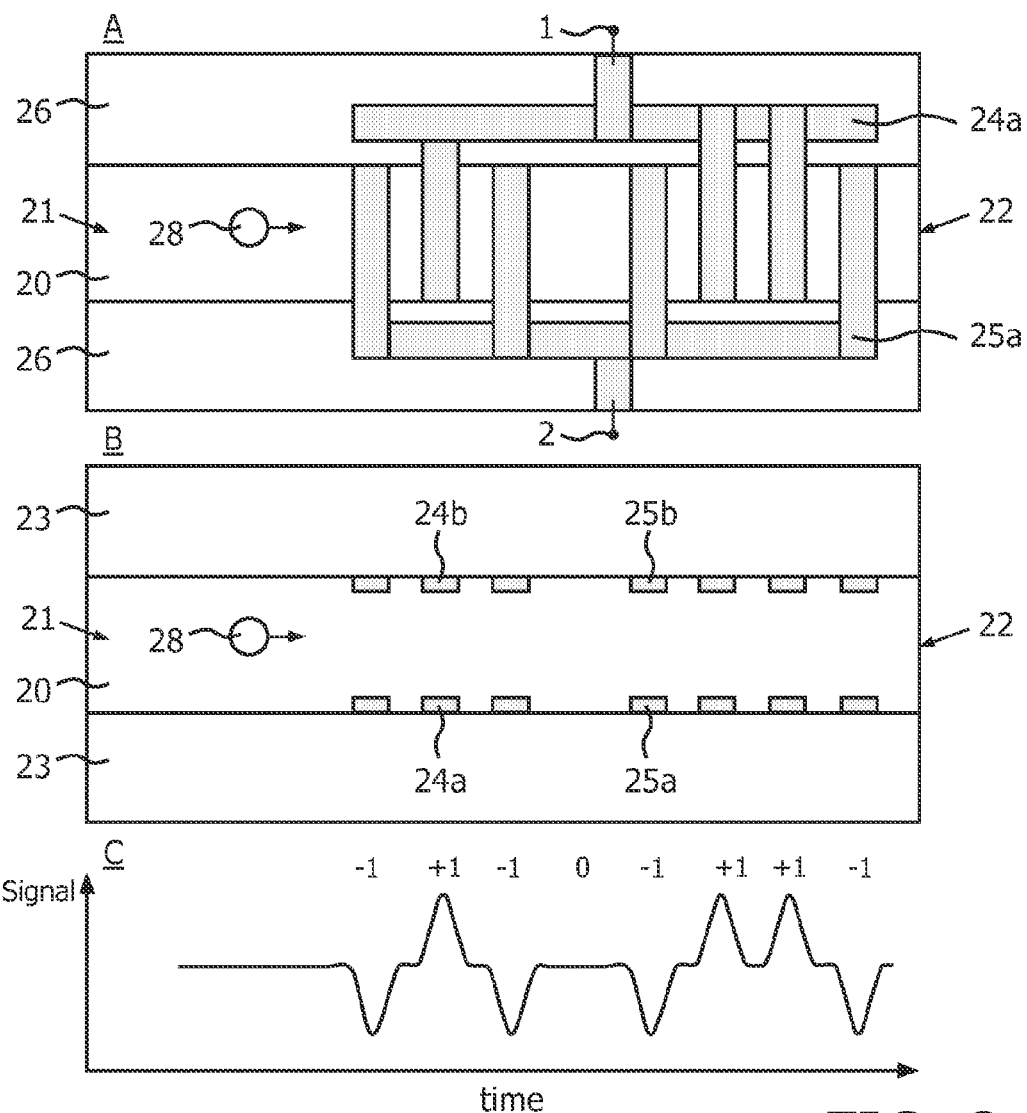
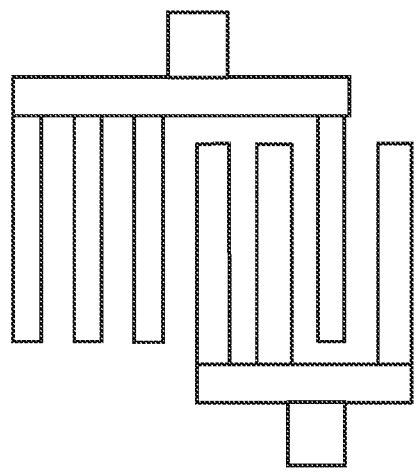
FIG. 3
FIG. 4

FINGERED ELECTRODES FOR MICROFLUIDIC SINGLE PARTICLE ANALYSIS

FIELD OF THE INVENTION

The invention relates to the field of investigation of particles, and more specifically to discrimination of particles, for example biological cells, by impedance spectroscopy in a measurement channel which encloses a carrier liquid for transporting the particles. The invention may be used in a micro fabricated flow cytometer.

BACKGROUND OF THE INVENTION

The healthcare trend to Point-of-Care devices using disposable cartridges and smaller device formats calls for a miniaturization of existing fluid based tests. The resulting need to analyze smaller fluid volumes has driven the development of micro fluidic chips to measure the properties of particles in solutions on a single particle basis.

The current state of the art principle for electrical particle analysis is the Coulter counter. Here particles in an electrolyte solution are drawn through a small aperture, separating two electrodes between which an electric current flows. The voltage applied across the aperture creates a "sensing zone". Particles which pass through the aperture displace their own volume of electrolyte and therefore change the impedance of the aperture. This change in impedance produces a pulse which is characteristic of the size of the particle. This apparatus enables to determine the size distribution and concentration of the particles in the fluid. Coulter counters have also been realized in a microfluidic format.

Microfluidics also enable to probe the impedance in a channel in a sideways fashion. Probing the fluid by opposing or adjacent electrodes inside a channel was consequently proposed. In macrofluidics, similar structures have been proposed inside an aperture, and with multiple electrode pairs.

Cheung et al. describe in "Impedance Spectroscopy Flow Cytometry: On-Chip Label-Free Cell Differentiation", Cytometry Part A 65A: 124-132 (2005), a microfluidic chip that uses two pairs of electrodes 10$a$, 11$a$ and 10$b$, 11$b$ inside a narrow microfluidic channel 12, as shown in FIG. 1. Here, while one of the electrode pairs senses the particle, the other pair acts as a reference.

Both top electrodes 11$a$, 11$b$ are connected to the same AC or DC input signal (A=B) while the bottom electrodes 10$a$, 10$b$ are connected to ground (signal C). The currents passing through the fluid in the micro fluidic channel 12 between the left and the right electrode pair are measured, and the corresponding impedances between the left and the right electrode pair are determined, amplified and their difference is taken by standard analog electronics. The in-phase and out-of-phase parts of the resulting AC signal are measured using standard Lock-in-technology. Without a particle passing the electrodes 10$a$, 11$a$; 10$b$, 11$b$ the determined difference signal is preferably, although not necessarily, zero (in practice always an offset may be present due to electronic component inaccuracies). If a particle 13 coming from the left passes first the left electrode pair 10$a$, 11$a$ a positive almost Gaussian shape like signal is produced when sensing the impedance difference between the electrode pairs. When the particle 13 afterwards passes the right electrode pair 10$b$, 11$b$ a negative Gaussian shape signal is produced when sensing the impedance difference between the electrode pairs. The resulting antisymmetric double Gaussian signal shape can be seen at the bottom part of FIG. 1.

The standard way to analyse the measurement, as also described in the reference mentioned above, is to use a thresholding algorithm to find the particle events. Only the amplitude of the double Gaussian signal is used. It is determined by simply taking the difference between the maximum and the minimum of the signal curve. The time delay T between maximum and minimum can be used to determine the speed of the particle 13.

SUMMARY OF THE INVENTION

It is an object of embodiments of the present invention to provide a device and method for performing particle investigation with good sensitivity.

The above objective is accomplished by a device and method according to the present invention.

Particular and preferred aspects of the invention are set out in the accompanying independent and dependent claims. Features from the dependent claims may be combined with features of the independent claims and with features of other dependent claims as appropriate and not merely as explicitly set out in the claims.

In a first aspect, the present invention provides a measurement device for investigating particles which are suspended in a carrier liquid. The measurement device comprises at least a first pair of measurement electrodes for carrying out an electrical measurement of the particles, wherein at least one electrode of the pair of measurement electrodes is a fingered electrode having a plurality of fingers.

In embodiments of the present invention, both electrodes of an electrode pair are fingered electrodes. In alternative embodiments of the present invention, one electrode of an electrode pair is a fingered electrode, while the other electrode is a non-fingered electrode, e.g. an electrode plate.

In embodiments of the present invention, both electrodes of an electrode pair are located at opposite sides of a microfluidic channel. In alternative embodiments, the electrodes of an electrode pair are located at a same side of a micro fluidic channel.

The investigation of particles suspended in a carrier liquid may lead to discrimination of such particles, e.g. one type of particles may be distinguished from another type of particles.

In particular embodiments of the present invention, the electrical measurement may be an impedance measurement.

A measurement signal obtained at the measurement electrodes may be cleaned up by standard signal processing techniques.

The pattern of fingered electrodes according to embodiments of the present invention creates a longer and more complicated signal shape than the signal shape obtained with prior art measurement devices with one measurement electrode finger and a reference electrode finger, which generates a double Gaussian signal shape. The longer signal shape obtained leads to a significant improvement in measurement sensitivity. The length and complexity of the signal shape depend on the number of fingers on the fingered electrode(s) of one pair, and on the number of pairs of measurement electrodes.

One application for the measurement device according to embodiments of the present invention is to significantly improve the measurement sensitivity of impedance measurements on blood cells, leading to a better differentiation between different types of particles, e.g. white blood cells. Better measurement sensitivity also enables the measurement of smaller particles, e.g. platelets or microparticles, and higher throughput. Moreover, maximum fluid flow speed of microfluidic devices is limited by the sensitivity of the detectors. Better sensitivity allows higher speed and hence higher throughput. More sensitive devices can therefore deliver results faster. Speed is one of the most important selling factors for medical devices, in particular hand held devices.

Another advantage is that with measurement devices according to embodiments of the present invention, even the detection of overlapping particles may be possible. Overlapping particles are particles which are in the sensing zone between the electrodes at the same time, so the measured signal is a superposition of the separate signals from both particles. This does not mean the particles have to enter the sensing zone at exactly the same time nor that they have the same speed. The fingered electrode arrangement makes it easier to detect both particles even if they are in the sensing zone at similar times. This is because although the signals are long in duration, the autocorrelation function is sharp and particles can be separated from each other if they are further away from each other than one electrode finger (if at the same speed), or at a significantly different speed. Overlapping particles are a common problem in state-of-the-art particle counters. State of the art electrical methods like the well-known Coulter Counter use either complicated fluid flow systems like sheath flow to avoid overlapping particles or use statistical methods to account for them. These add expense and bulk to the system. Higher dilution of the sample reduces this issue, but increases both measurement time and the bulk of reagents used. It is an advantage of embodiments of the present invention that lower sample dilutions can be used, reducing the time for the test to be performed, and lowering the bulk of reagents needed. These are important advantages for point-of-care devices, which need to be small and fast.

In a measurement device according to embodiments of the present invention, the fingers may be accommodated so as to have a pattern that defines a sequence code that defines good autocorrelation properties. A good autocorrelation property is normalised so that the maximum is always one, and the correlation value when shifted is less. The ratio of the maximum to the correlation values when shifted defines the signal to noise ratio gain. The pattern of the fingers may correspond to a pseudorandom number sequence.

A measurement device according to embodiments of the present invention may furthermore comprise a second pair of measurement electrodes. Such second pair of measurement electrodes may be used as a reference to get rid of the offset in the measurement signal. In embodiments of the present invention, more than two measurement electrode pairs may be provided.

In embodiments of the present invention, the second pair of measurement electrodes may also be a pair of electrodes of which at least one is a fingered electrode. In embodiments of the present invention, the fingers of one electrode of the first pair of electrodes may be interdigitated with the fingers of one electrode of the second pair of electrodes. This has the advantage that measurement signals with three values possible: −1, 0, 1.

In embodiments of the present invention, the second electrodes of both electrode pairs may be combined electrodes, i.e. they may be one and the same electrode for both electrode pairs, e.g. a plate electrode.

In a second aspect, the present invention provides a microfluidic system comprising a measurement device according to embodiments of the present invention. A measurement device according to embodiments of the present invention may be a component of an integrated microfluidic lab-on-chip device. It may be integrated for example in a point-of-care and/or handheld device.

In a further aspect, the present invention provides a cell sorter comprising a microfluidic system according to embodiments of the present invention.

A measurement device according to embodiments of the present invention may be used for analysis of body fluids such as for example blood, saliva or urine. It is easy to combine with particle sorting structures. An example is rare cell enrichment.

In yet another aspect, the present invention provides a method for investigating particles suspended in a carrier liquid. The method comprises carrying out an electrical measurement process on at least one particle using at least one measurement electrode pair of which at least one electrode is a fingered electrode having a plurality of fingers, thus generating a measurement signal, and determining from the measurement signal presence of a particle in the carrier liquid. The investigation of particles may lead to discrimination of particles.

In embodiments of the present invention, carrying out an electrical measurement process may comprise impedance measuring. Carrying out an electrical measurement process may comprise impedance spectroscopy.

A method according to embodiments of the present invention may further comprise carrying out a reference measurement, and comparing a result of the reference measurement with the measurement signal.

In a method according to embodiments of the present invention, determining from the measurement signal presence of a particle in the carrier liquid may comprise correlating a model curve describing passage of a particle between the fingers of the at least one measurement electrode pair with a section of the measurement signal.

The above and other aspects of the invention will be apparent from and elucidated with reference to the embodiment(s) described hereinafter.

BRIEF DESCRIPTION OF THE DRAWINGS

FIG. 3 schematically illustrates an interdigitated electrode structure according to embodiments of the present invention; (A) bottom view according to line A-A' in FIG. 2, where a particle is shown to flow through the structure from left to right, (B) cross-sectional side view according to line B-B' in FIG. 2, and (C) idealized resulting lock-in output signal.

FIG. 4 illustrates an embodiment of an interdigitated fingered electrode structure as can be used with embodiments of the present invention, which interdigitated fingered electrode structure is arranged in accordance with a Barker code with length 7.

Figure 1:
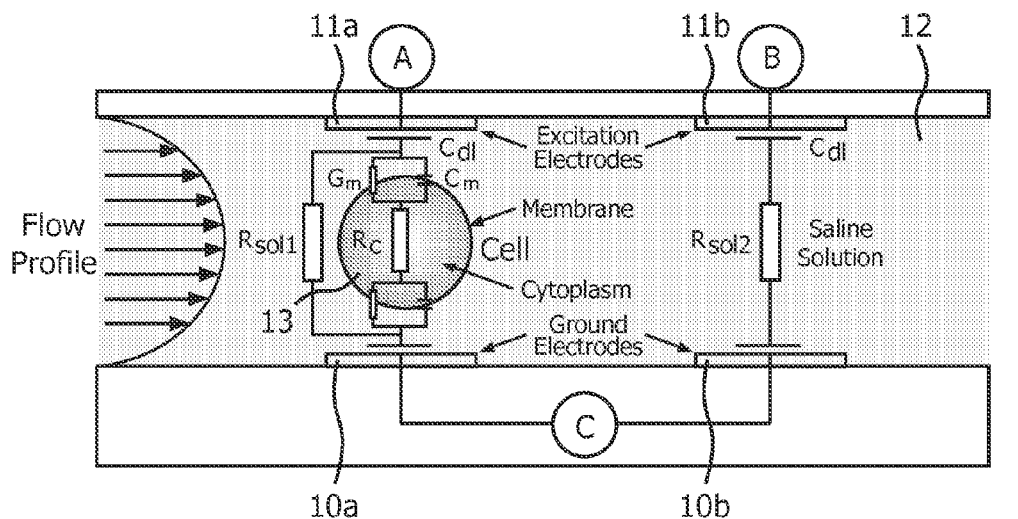
FIG. 1 illustrates (top) a diagrammatic side view of a microfluidic channel showing a sample cell passing between the measurement and reference electrode pair in accordance with the prior art; and (bottom) the cell signal which is the output of a lock-in amplifier measuring the current difference between both electrode pairs.

The drawings are only schematic and are non-limiting. In the drawings, the size of some of the elements may be exaggerated and not drawn on scale for illustrative purposes.

In the different drawings, the same reference signs refer to the same or analogous elements. Any reference signs in the claims shall not be construed as limiting the scope.

DETAILED DESCRIPTION OF ILLUSTRATIVE EMBODIMENTS

In one aspect, the present invention relates to a measurement device for investigating, for example discriminating, particles which are suspended in a carrier liquid. In embodiments of the present invention, the suspended particles may be biological cells such as e.g. red blood cells, white blood cells or platelets; however, the present invention is not limited to blood cells or other biological cells and may be used with particles of a non-biological nature without departing from the scope of the present invention as defined by the appended claims.

Figure 2:
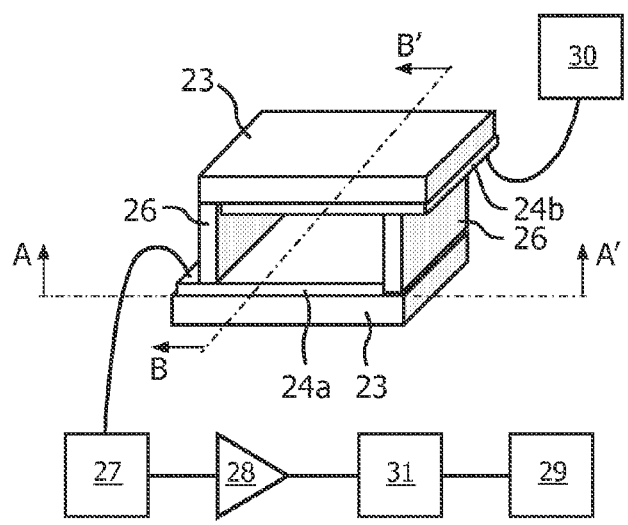
FIG. 2 is a schematic 3D view of a microfluidic channel according to embodiments of the present invention, coupled to a signal generator and a measurement circuit, illustrated in block diagram.

As schematically illustrated in FIG. 2 and its cross-sections as for example illustrated in FIG. 3, parts A and B, a measurement device according to embodiments of the present invention comprises a microfluidic channel 20. The microfluidic channel 20 is arranged for allowing therethrough flow of the carrier liquid containing suspended particles. To this end, the microfluidic channel 20 is provided with an inlet 21 for receiving the carrier liquid and the suspended particles, and an outlet 22 for evacuating the carrier liquid and the suspended particles.

The microfluidic channel 20 may be manufactured using standard semiconductor processes, e.g. standard CMOS technology processes. The microfluidic channel 20 may be fabricated on a suitable substrate 23, e.g. a glass substrate, onto which at least one pair of conductive electrodes 24a, 24b; 25a, 25b, e.g. metal electrodes, are patterned, for example by lift-off. In embodiments of the present invention, the electrodes are made of biologically inert materials such as for example titanium or platinum. The at least one pair of electrodes comprises at least a first measurement electrode pair, the electrodes 24a, 24b of the measurement electrode pair in the embodiment illustrated being located at opposite sides of the microfluidic channel 20. According to embodiments of the present invention, both electrodes 24a, 24b of the first measurement electrode pair are fingered electrodes. In embodiments of the present invention, the fingered electrodes may be such that the fingers of one electrode are spatially placed irregularly adjacent each other in flow direction of the carrier liquid through the micro fluidic channel 20. With "spatially placed irregularly" is meant that the electrode fingers of one electrode are not placed in a spatially regular pattern. This means that there is at least one location where one would expect to have an electrode finger of a particular electrode where no actual electrode finger of that electrode is provided. This way, the electrode fingers are provided according to a pattern that defines a sequence code. In accordance with embodiments of the present invention, the sequence code of the electrode fingers is chosen for good autocorrelation properties. A good autocorrelation property is normalised so that the maximum is always 1, and the value when shifted is less. The ratio of the maximum to the values when shifted defines the signal to noise ratio gain, so it will typically be about 1/m for a m-bit sequence. Such good autocorrelation property may be obtained by providing a pattern of the fingers corresponding to a pseudorandom number sequence.

Figure 8:
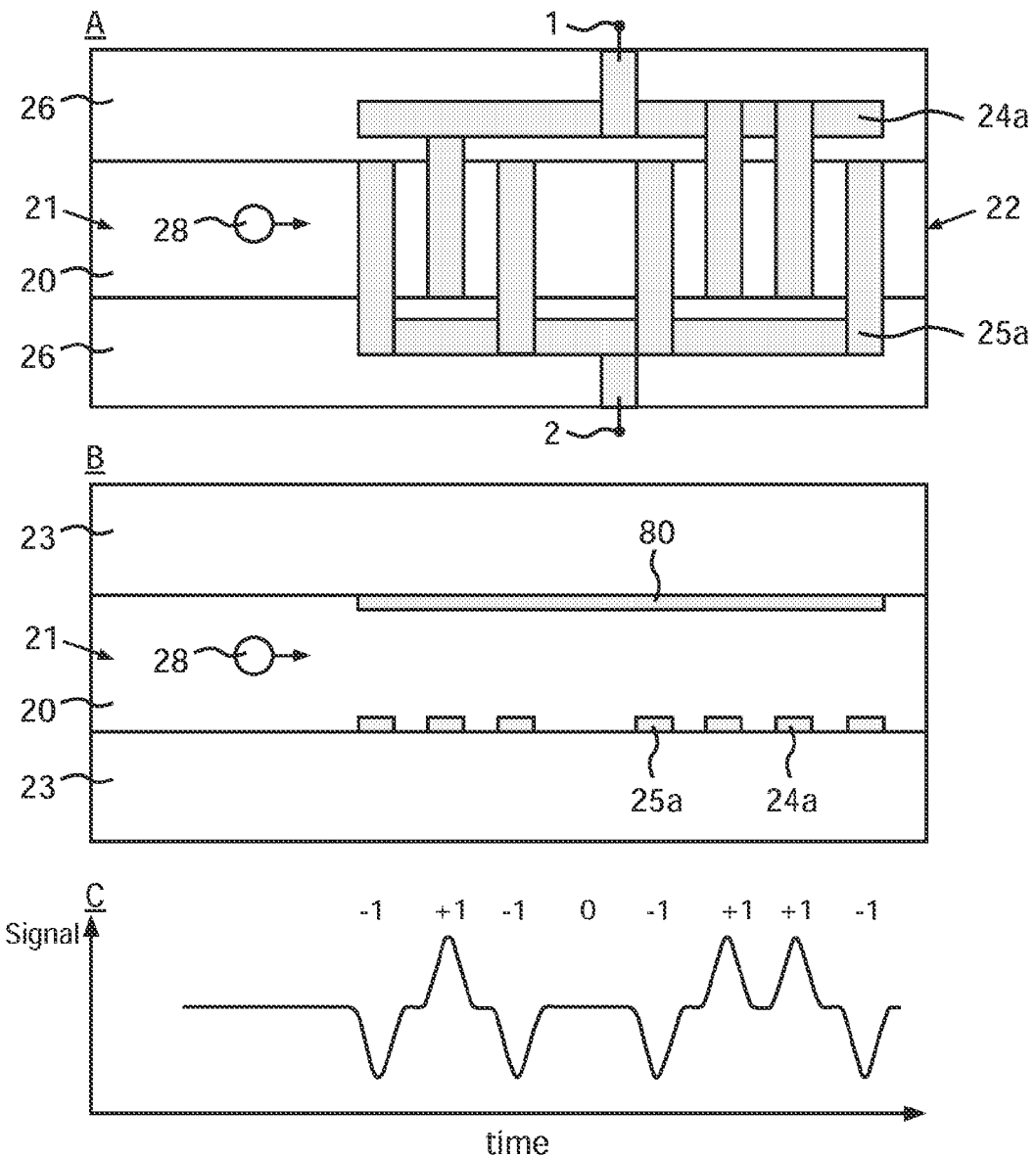
FIG. 8 schematically illustrates an interdigitated electrode structure according to further embodiments of the present invention; (A) bottom view according to line A-A' in FIG. 2, where a particle is shown to flow through the structure from left to right, (B) cross-sectional side view according to line B-B' in FIG. 2 and (C) idealized resulting lock-in output signal.

In embodiments of the present invention, at least two pairs of measurement electrodes are provided, at least a first measurement electrode pair 24a, 24b and a second measurement electrode pair 25a, 25b. At least one electrode of the first measurement electrode pair is a fingered electrode. In embodiments of the present invention, at least one electrode of the first measurement electrode pair and at least one electrode of the second measurement electrode pair may be fingered electrodes, while the other electrodes of the measurement electrode pairs do not need to be fingered. In embodiments of the present invention, one electrode of the first measurement electrode pair and one electrode of the second electrode pair are fingered electrodes, and the second electrodes of both measurement electrode pairs are not fingered. The second electrodes of both measurement electrode pairs may even be one and the same electrode. Such embodiment is illustrated in FIG. 8.

In alternative embodiments of the present invention, both the electrodes of the first measurement electrode pair 24a, 24b and the electrodes of the second measurement electrode pair 25a, 25b are fingered electrodes, as illustrated in FIG. 3. The electrodes of the first measurement electrode pair 24a, 24b and the electrodes of the second measurement electrode pair 25a, 25b may be interdigitated electrodes.

After patterning of the electrodes, sidewalls 26 may be patterned on the substrate 23. The sidewalls may be made from any suitable material, for example epoxy or resist such as polyimide or SU8. Two similar wafers, each comprising a substrate, electrodes and sidewalls, may be bonded face to face to create closed channels 20 that have electrodes 24a, 24b and optionally electrodes 25a, 25b on the top and bottom walls 23. The chips may be diced from the wafer pair so that the conductive contacts to the electrodes 24a, 24b; 25a, 25b on both sides can be accessed, e.g. by using spring-loaded connectors.

The first electrodes 24a, 25a of the measurement electrode pairs are connected to a sensing device 27, e.g. sensing electronics, for measuring a resulting measurement signal. The measurement signal may be an electrical signal such as a current signal or a voltage signal. The measurement device may measure the current flowing or voltage difference existing between the electrodes of a measurement electrode pair. Standard deconvolution techniques may be used to detect the signals, and show an improved sensitivity.

The measurement device according to embodiments of the present invention may optionally be connected up to an amplifier 28 for amplifying the measurement signal. The measurement signal, before or after amplification, may be used to determine the impedance mismatch between the electrodes of an electrode pair 24a, 24b; 25a, 25b. This determined impedance mismatch changes if a particle 28 passes between the electrode fingers of an electrode pair.

A device according to embodiments of the present invention may furthermore comprise a lock-in amplifier 31 for extracting the measurement signal from its noisy environment. A device according to embodiments of the present invention may furthermore comprise signal evaluator 29 for evaluating the determined impedance signal. The evaluation of the determined impedance signal may lead to investigation and ultimately to discrimination of particles passing over or between the electrodes.

Once the measurement signal is obtained, the particles can be distinguished by multiple parameters derived from the signal, for example amplitude or phase of the signal. For low AC frequencies, e.g. from DC to frequencies up to 500 kHz, the amplitude for example may be equivalent to the cell size. In case of measurements with two superimposed AC input signals with different frequencies the ratio of the amplitudes at the two frequencies can distinguish particles of the same physical size by determining the inner conductivity or the capacitance of the particles.

Using the fingered electrodes according to embodiments of the present invention simplifies the analog electronics as signal detection gets easier. This decreases the manufacturing cost of the measurement devices.

FIG. 3, parts A and B, diagrammatically illustrate a bottom view and a cross-sectional side view, respectively, of a first embodiment of a measurement device according to embodiments of the present invention.

In this embodiment, the measurement device comprises a microfluidic channel 20 and two electrode pairs 24a, 24b; 25a, 25b. Both electrodes of each electrode pair are fingered electrodes, as can be seen in parts A and B of FIG. 3. The electrodes of each electrode pair are located at opposite sides of the microfluidic channel 20, e.g. top and bottom, as is best illustrated in part B of FIG. 3. The fingered electrodes of both electrode pairs are interdigitated according to a predetermined pattern. In the embodiment illustrated in FIG. 3, the patterns of the fingered electrodes 24b, 25b and 24a, 25a on the top and on the bottom, respectively, of the channel 20 are equal. This is not necessary. In alternative embodiments of the present invention, the electrodes driven by common signals may be replaced wholly or in part by a larger single electrode. An example thereof is illustrated in FIG. 8. In this embodiment, an interdigitated electrode structure 24a, 25a is provided on the bottom of the channel 20, and a single electrode 80 is provided on the top of the channel 20.

In the embodiment of FIG. 3, the two electrodes 24b, 25b at the top of the microfluidic channel 20 are connected to a signal generator 30 (not illustrated in FIG. 3). They may both be connected to the same signal generator. In the alternative embodiment of FIG. 8, the single top electrode 80 is connected to a signal generator 30. In both embodiments illustrated, the two electrodes at the bottom of the microfluidic channel are connected to a sensing device 27, e.g. to sensing electronics.

In alternative embodiments, similar in structure to the one of FIG. 3, i.e. with two pairs of measurement electrodes, a first electrode of a first measurement electrode pair, which first electrode is located at the top of the microfluidic channel, may be connected to a signal generator and the second electrode of the first measurement electrode pair which is located at the bottom of the microfluidic channel may be connected to a sensing device. A first electrode of the second measurement electrode pair, which first electrode is located at the bottom of the microfluidic channel, may also be connected to a signal generator, and the second electrode of the second measurement electrode pair which is located at the top of the microfluidic channel may be connected to a sensing device. This means that, in embodiments of the present invention, the signal electrodes and the sensing electrodes may be inversed and do not have to be at the same side of the channel for different electrode pairs.

In the embodiment illustrated in FIG. 3, measurement signals are measured at the bottom electrodes of the first and the second electrode pair 24a, 24b; 25a, 25b. The difference of both measurement signals may optionally be amplified in amplifier 28 and fed into a lock-in amplifier 31.

A lock-in amplifier 31 takes the input signal, e.g. the measurement signal, optionally amplified by the amplifier 28, multiplies it by a reference signal having a known signal shape (either provided from an internal oscillator or an external source), and integrates it over a specified time, usually in the order of microseconds to a few seconds, depending on the bandwidth of the lock-in amplifier. Long integration times reject more noise, but only allow slow signals, i.e. slow measurement of events. There thus is a fundamental speed-noise trade-off in selecting the lock-in integration time or bandwidth.

The resulting signal is a low frequency signal, where the contribution from any signal that is not at the same frequency as the reference signal is attenuated essentially to zero, as well as the out-of-phase component of the signal that has the same frequency as the reference signal (because sine functions are orthogonal to the cosine functions of the same frequency). This is why a lock-in amplifier is a phase sensitive detector.

For a sine reference signal and an input waveform Uin(t), the DC output signal Uout(t) can be calculated for an analog lock-in amplifier by:

$$U_{out}(t) = \frac{1}{T}\int_{t-T}^{t} \sin[2\pi f_{ref} \cdot s + \phi]U_{in}(s)\,ds$$

where φ is a phase that can be set on the lock-in amplifier 31 (set to zero by default).

Practically, many applications of the lock-in amplifier only require recovering the signal amplitude rather than relative phase to the reference signal; a lock-in amplifier usually measures both in-phase (X) and out-of-phase (Y) components of the signal and can calculate the magnitude (R) from that.

The resulting theoretical in-phase signal obtained from the lock-in amplifier 31 is shown in part C of FIG. 3. The signal can be interpreted as a digital code consisting out of values −1 (when a particle comes across a finger of a first electrode pair), 0 (when a particle comes across a position where no fingers of the electrode pairs are provided) and 1 (when a particle comes across a finger of a second electrode pair). The out-of-phase signal looks similar but has a different amplitude.

In telecommunications, direct-sequence spread spectrum (DSSS) is a known modulation technique. As with other spread spectrum technologies, the transmitted signal takes up more bandwidth than the information signal that is being modulated. The name 'spread spectrum' comes from the fact that the carrier signals occur over the full bandwidth (spectrum) of a device's transmitting frequency.

Direct-sequence spread-spectrum transmissions multiply the data being transmitted by a "noise" signal. This noise signal is a pseudorandom sequence of 1 and −1 values, at a frequency much higher than that of the original signal, thereby spreading the energy of the original signal into a much wider band.

The resulting signal resembles white noise, like an audio recording of "static". However, this noise-like signal can be used to exactly reconstruct the original data at the receiving end, by multiplying it by the same pseudorandom sequence (because 1×1=1, and −1×−1=1). This process, known as "despreading", mathematically constitutes a correlation of the transmitted PN (pseudo-noise) sequence with the receiver's assumed sequence.

For de-spreading to work correctly, the transmit and receive sequences must be synchronized. This requires the receiver to synchronize its sequence with the transmitter's sequence via some sort of timing search process. However, this apparent drawback can be a significant benefit: if the sequences of multiple transmitters are synchronized with each other, the relative synchronizations the receiver must make between them can be used to determine relative timing, which, in turn, can be used to calculate the receiver's position if the transmitters' positions are known. This is the basis for many satellite navigation systems.

The resulting effect of enhancing signal to noise ratio on the channel is called processing gain. This effect can be made larger by employing a longer PN sequence, but physical devices used to generate the PN sequence impose practical limits on attainable processing gain.

If an undesired transmitter transmits on the same channel but with a different PN sequence (or no sequence at all), the de-spreading process results in no processing gain for that signal. This effect is the basis for the code division multiple access (CDMA) property of DSSS, which allows multiple transmitters to share the same channel within the limits of the cross-correlation properties of their PN sequences.

In accordance with embodiments of the present invention, the fingers of the electrode pairs 24a, 24b; 25a, 25b are located such that the resulting signal is similar to a pseudo noise (PN) code in direct-sequence spread spectrum (DSSS). But different is that the sequence cannot change and that the signal is not synchronized. It is like transferring just one bit of data but determining the point of time when it was transmitted. Therefore, according to embodiments of the present invention, the appearance of the signal has to be checked by fitting a model curve (similar to the theoretical signal in part C of FIG. 1) to a moving section of the measurement signal.

In accordance with embodiments of the present invention, at the same particle speed the resulting signals are longer and more complicated (having a bigger bandwidth) than signals obtained according to the prior art with two non-fingered electrode pairs. Standard deconvolution techniques applied on signals measured according to embodiments of the present invention therefore show an improved sensitivity.

As illustrated above with respect to FIG. 3, the code sequence can be a three level sequence (−1, 0, 1), as gaps between the electrodes can be used as well as the electrodes that will give positive or negative pulses. This gives further options for code optimisation. In alternative embodiments, a two level sequence can be obtained.

The performance of the technique is complicated by the fact that the flow profile inside a microfluidic channel is parabolic. Therefore particle speeds at different locations of a cross-section of the microfluidic channel 20 can be different, which leads to an additional fit parameter. The additional fit parameter may be the speed of the event, in addition to the time of the event. In radio systems everything is slow compared to the speed of light, so one only needs to find events in time. Particles at different speeds lead to signals which are stretched out differently in time.

While in DSSS the noise is independent of the code length, in embodiments of the present invention the noise goes up with the probed fluidic volume. As the fluidic volume goes up with the number of (optionally interdigitated) electrode fingers (=N) the noise goes up with sqrt(N). The ability of the autocorrelation technique to reject noise scales linearly with the bit length M, which due to the inclusion of zeros can be higher than the number of electrode fingers N, so the ability to extract signal from noise is improved by ~M/sqrt(N). Thus, for example a 13 electrode sequence with an equal number of suitably arranged gaps would give an effective gain of ~7.2 in effective signal to noise. The longer the coding sequence is, the bigger the enhancement on signal to noise ratio. Hence it is more advantageous to have more fingers in the fingered electrodes.

The Pseudo Noise (PN) codes used in accordance with embodiments of the present invention require certain mathematical properties. The key property is that the sequence has good, e.g. maximum, auto-correlation when the sequences are aligned in time, but low, e.g. ideally zero, autocorrelation when shifted in time. Known examples of these are Barker Codes and Willard Codes. A Barker Code is a sequence of N values $a_j$ of +1 and −1, aj for j=1, ..., N, such that $$\left| \sum_{j=1}^{N-\alpha} a_j a_{j+\alpha} \right| \leq 1$$

for all $1 \leq \alpha < N$. An example of a Barker code of length 7 is +1+1+1−1−1+1−1, which would correspond to an interdigitated fingered structure as for example illustrated in FIG. 4.

Figure 9:
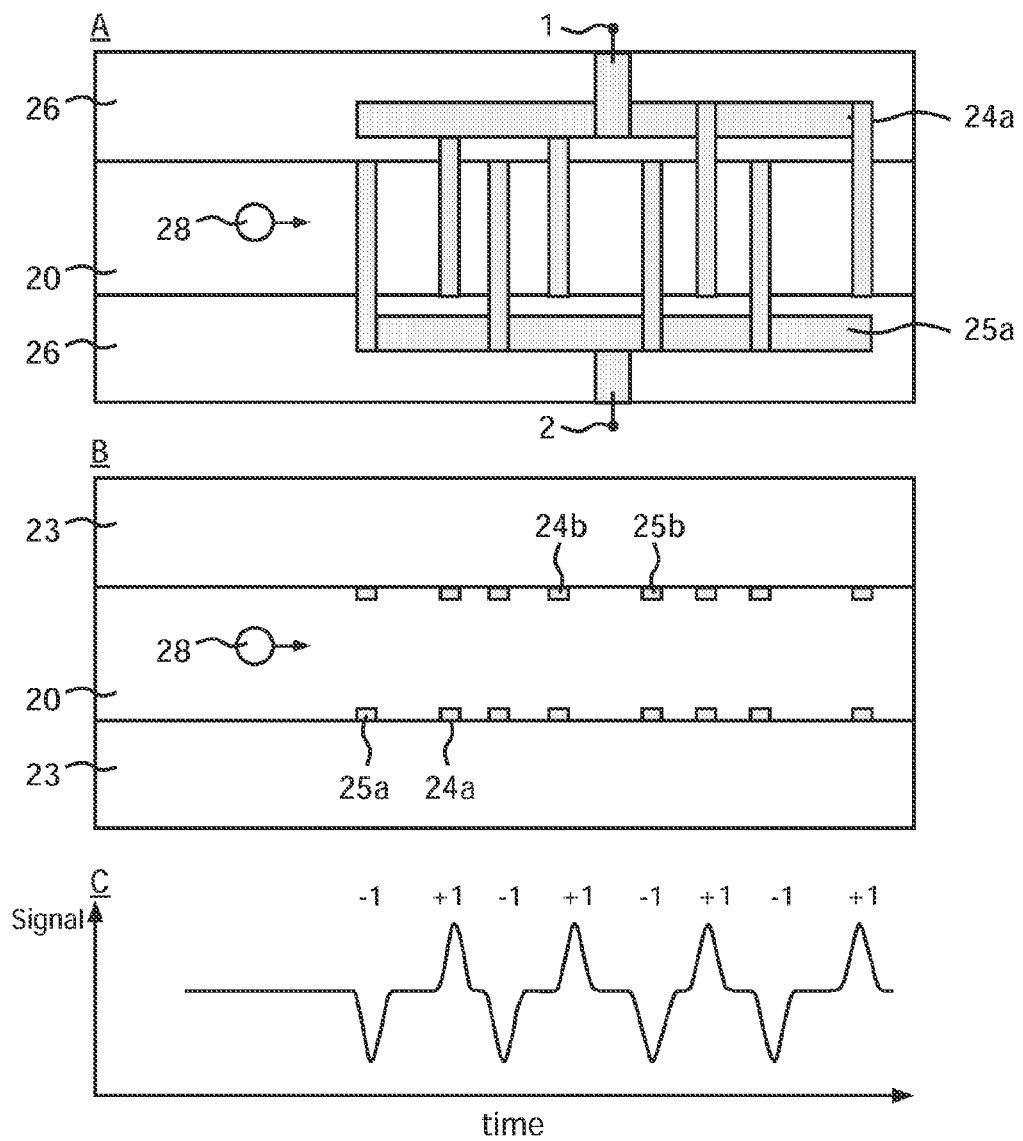
FIG. 9 schematically illustrates an interdigitated electrode structure according to further embodiments of the present invention, where the code is varied by varying spaces between the electrode fingers; (A) bottom view according to line A-A' in FIG. 2, where a particle is shown to flow through the structure from left to right, (B) cross-sectional side view according to line B-B' in FIG. 2 and (C) idealized resulting lock-in output signal.

For the technique as used in microfluidics in accordance with embodiments of the present invention, it is additionally advantageous for code optimisation if the signal has good autocorrelation properties when used with different timescales. This requirement, if met, allows to distinguish particles of different speeds, even when multiple particles are in the electrode region. This requirement may be met by including many more zeros in the code sequence (i.e. having mostly spaces between fingers and only a few electrode fingers) leading to the autocorrelation properties in both time and space being much better. The downside is a need for a physically longer channel 20, and in radio systems this is not practical as it would take longer to transmit each bit. So a sequence as for example illustrated in FIG. 9 is a good embodiment of a device according to the present invention if the electrode fingers are narrow compared to the spaces between them. This may be obtained either by making the spaces between the electrode fingers bigger, or by making the electrodes narrower. In practice, the electrode length is preferably similar to the height of the channel, so increasing the gap is a particularly advantageous solution.

Figure 5:
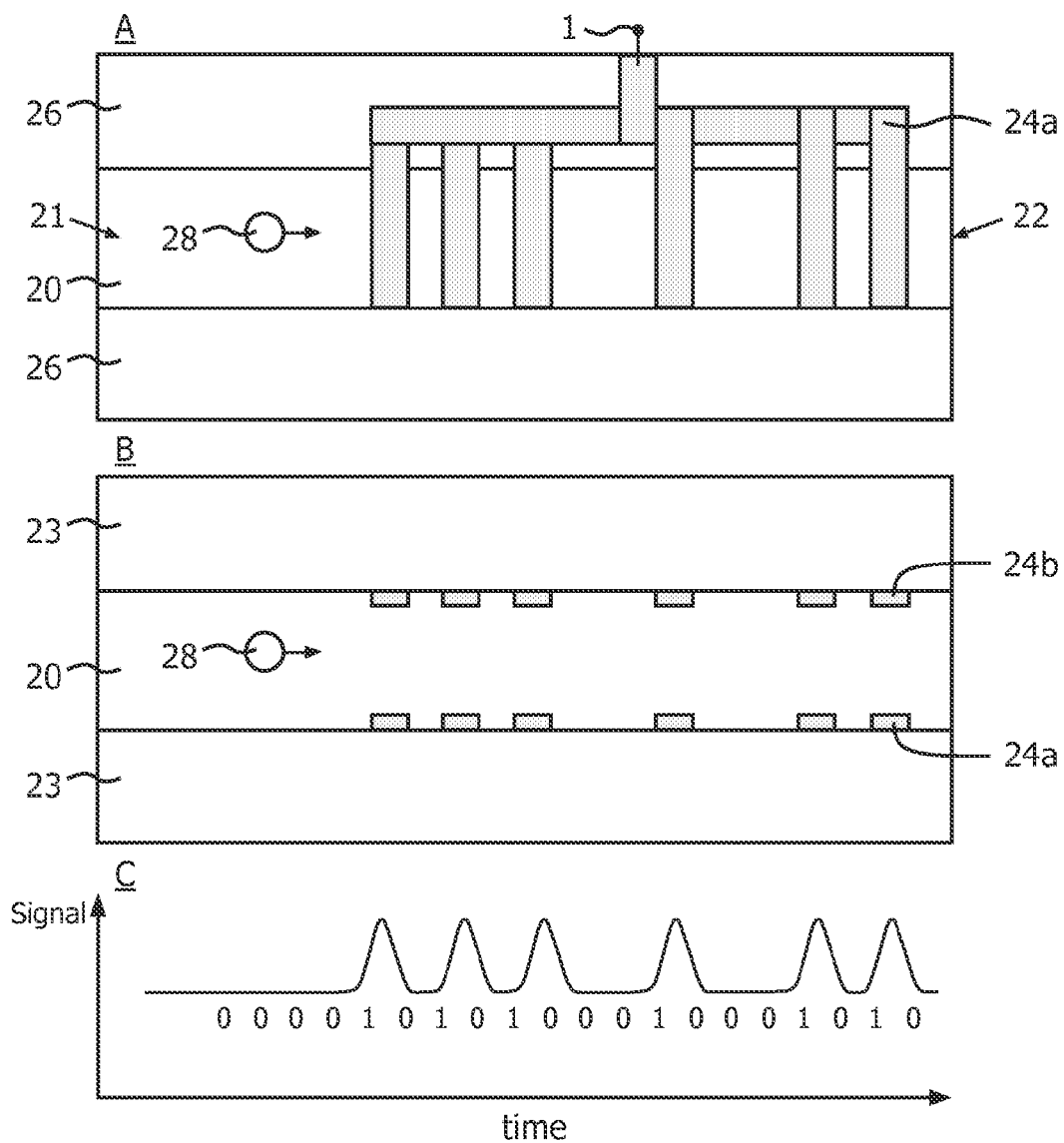
FIG. 5 schematically illustrates a fingered electrode structure according to a further embodiment of the present invention; (A) top view, where a particle is shown to flow through the structure from left to right, (B) cross-sectional side view, and (C) idealized resulting lock-in output signal.

In a further embodiment of the present invention, as illustrated in FIG. 5, it is possible to leave away the second measurement electrode pair. In that case, only a single measurement electrode pair 24a, 24b is provided. In the embodiment illustrated, the electrodes of the pair are located at opposite sides of the microfluidic channel 20. According to embodiments of the present invention, both electrodes of the electrode pair are fingered. In this case, the code does not average to zero, but the average is known: an offset in the measurement signal is given by conductivity of the fluid without the particle. To get rid of the offset in the measurement signal, electronic means can be used, for example by using a low pass filtered signal as a baseline, to subtract the average. For a single fingered electrode pair 24a, 24b measuring the impedance of the channel 20, that means the measured signal becomes a plurality of subsequent positive Gaussian like peaks.

Using now a fingered electrode structure and leaving out certain fingers as shown in parts A and B of FIG. 5, i.e. creating gaps between the fingers, leads to a measured sequence of single Gaussian peaks which can be detected by similar means as described above. Now the created sequence is similar to a purely binary code consisting of a sequence of values one and zero.

According to a further embodiment of the present invention, the measurement device may comprise at least one fingered electrode structure, wherein the electrode structure has a variable electrode finger width and/or variable spacing width.

Figure 10:
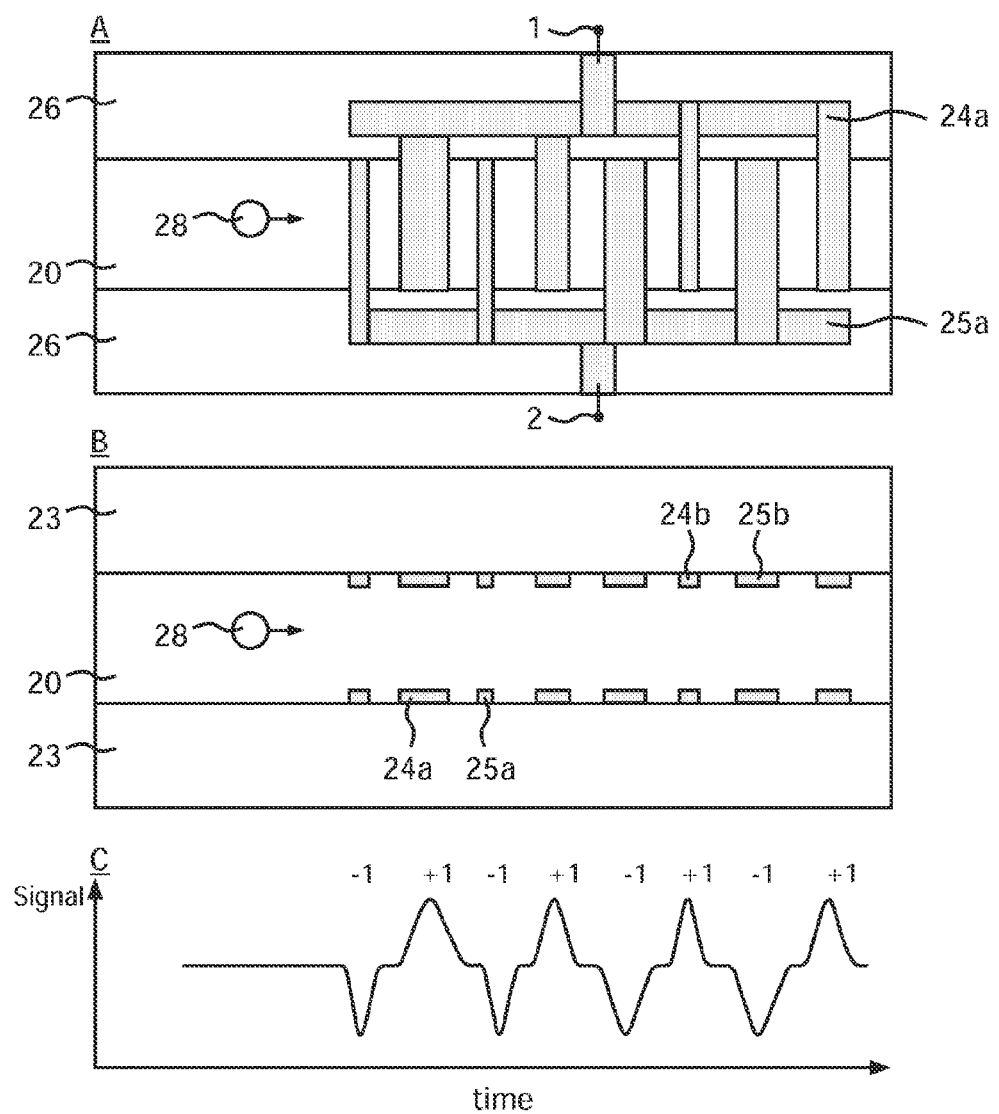
FIG. 10 schematically illustrates an interdigitated electrode structure according to further embodiments of the present invention, where the code is varied by varying the width of the electrode fingers; (A) bottom view according to line A-A' in FIG. 2, where a particle is shown to flow through the structure from left to right, (B) cross-sectional side view according to line B-B' in FIG. 2 and (C) idealized resulting lock-in output signal.

Examples are illustrated in FIG. 9, where the code is varied by spatially varying the spaces between the electrode fingers, and in FIG. 10, where the code is varied by spatially varying the width of the electrodes.

Figure 11:
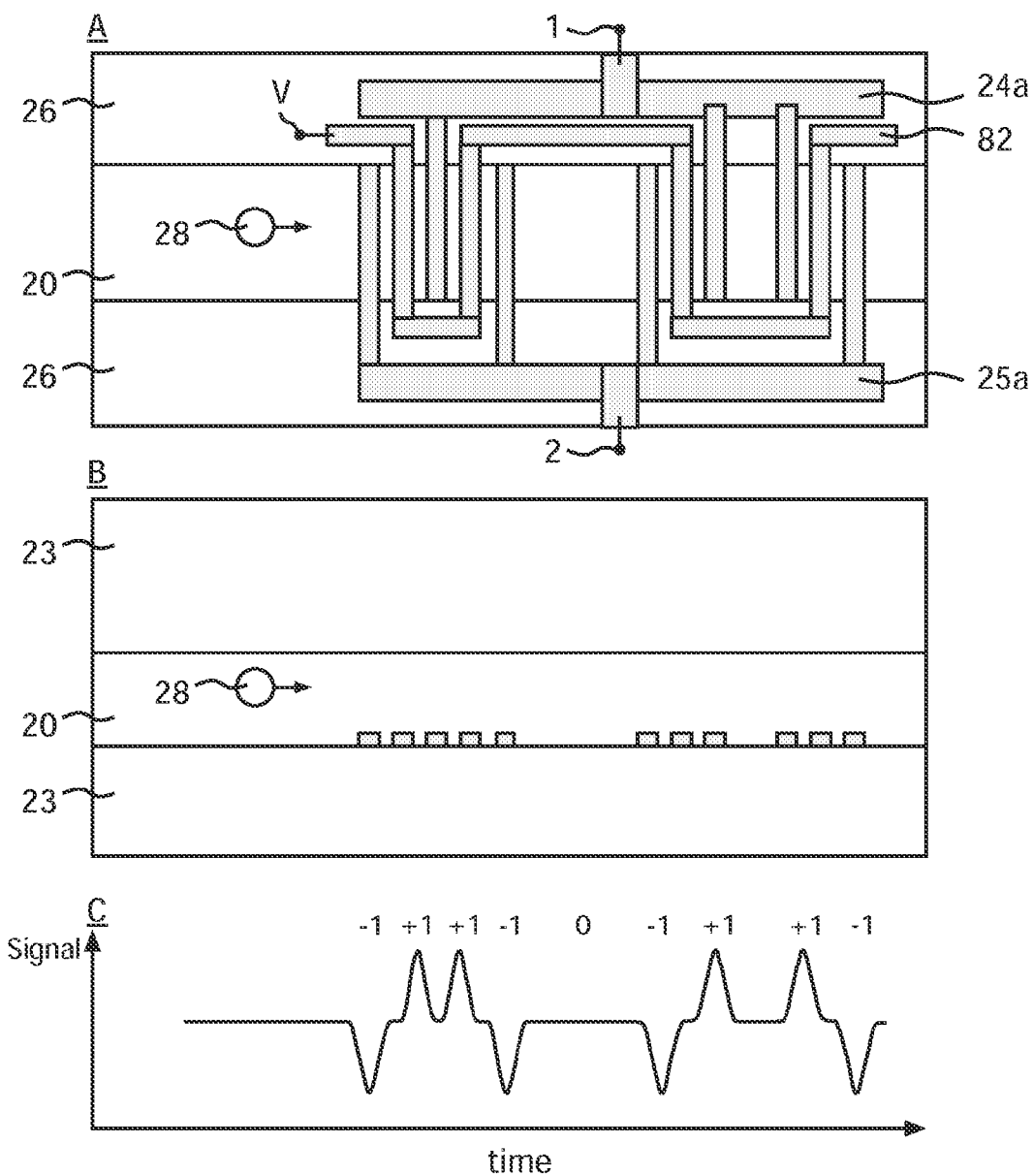
FIG. 11 schematically illustrates a fingered electrode structure according to embodiments of the present invention with all electrodes on the same side of the channel; (A) bottom view, where a particle is shown to flow through the structure from left to right, (B) cross-sectional side view, with vertical scale exaggerated compared to horizontal scale, and (C) idealized resulting lock-in output signal.

According to a further embodiment of the present invention, both electrodes of the measurement electrode pairs may be located at the same side of the channel 20. This is illustrated in FIG. 11. In the embodiment illustrated, a first measurement electrode pair 24a, 82 and a second measurement electrode pair 25a, 82 are provided. The first electrodes 24a, 25a are fingered electrodes which are interdigitated. The second electrodes of the first and second measurement electrode pair is a common electrode 82 which is routed between the fingers of the interdigitated first electrodes of both pairs.

The resulting theoretical in-phase signal obtained from the lock-in amplifier 31 is shown in part C of FIG. 11. The signal can be interpreted as a digital code consisting out of values −1 (when a particle comes between a finger of the first electrode of the second electrode pair and the common second electrode), 0 (when a particle comes across a position between two fingers of a same electrode) and 1 (when a particle comes between a finger of the first electrode of the first electrode pair and the common second electrode).

According to still another embodiment of the present invention (not illustrated), to get rid of the offset in the measurement signal due to electronic component inaccuracies a reference electrode may be put in a part of the microfluidic channel 20 which is physically shielded from the particle stream (and therefore never a particle passes it). With at least one electrode of the measurement electrode pair 24a, 24b being a fingered electrode, this has the same effect that the measured signal becomes a sequence of positive Gaussian like peaks.

A full blood count (FBC) contains a measurement of platelets (PLTs) as well as red blood cells (RBCs) and various white blood cells (WBCs). The measurement of RBC and WBCs with methods according to embodiments of the present invention is relatively straightforward as the cells are relatively large (>7 μm) and the signal spikes that occur as the cell passes over the fingers of the electrodes can be easily distinguished over the background noise. The average diameter of the platelets however is typically 2.4 times smaller than the diameter of red blood cells. Because the impedance spectroscopic measurement is volume related, the typical platelet signal is $1/15$ smaller than the RBC signal. In low cost systems, in which chip manufacturing tolerances and (analog) electronic complexity are kept to a minimum, the platelet spikes can drop below the noise level of the signal.

In the special case of the analysis of white blood cells by impedance measurements the signal to noise ratio limits the differentiation to the three main white blood cell types, namely monocytes, granulocytes and lymphocytes. The new device design according to embodiments of the present invention enables the differentiation between five or even more blood cell types.

It is therefore proposed according to further embodiments of the present invention to use template matching (correlation), using the template match (as measured by a correlation coefficient) as event trigger and restricting acceptance of the event by template parameters, as a means to record platelet events.

An analytical model curve being described by a sequence of Gaussian curves as defined by the fingered electrodes in accordance with embodiments of the present invention is correlated with a section of the measurement signal to find particles. Here a particle is detected by the resulting correlation coefficient exceeding a certain threshold. Only a section of the measured signal is correlated with the model curve at a time and the selected section moves along the measured signal in time. Due to speed variations of the particles each section has to be correlated with multiple possible model curves. This results into a procedure that essentially fits the model curve to the signal section by optimizing the model curve parameters. The resulting correlation coefficient is a measure how good the section can be described by the model curve. This method leads to a more accurate determination of the amplitude of the signal.

The above cross-correlation signal analysis is applicable, not only with the fingered electrodes as in accordance with the present invention, but also with the double Gaussian signal shape as known from the prior art. In that case, an analytical curve being described by two antisymmetric Gaussian curves is correlated with a second to the measurement signal to find particles. This method is limited by the simple (double Gaussian) shape of the signal which limits the sensitivity of the method as well as its ability to detect particles even below the signal noise.

As an example, the method is illustrated for a two-peak case comprising two antisymmetric Gaussian curves. Extension to multiple peaks lies within the skills of a person skilled in the art.

As template function, two point spread functions around $t_0$ may be used, separated by $2t_\delta$ with a width $\sigma = \omega t_\delta$ with a non-standard normalisation factor $$g_{t_0, t_\delta, \sigma}(t) = \frac{1}{\sqrt{2(1-e^{-t_\delta^2/\sigma^2})\sqrt{\pi\sigma^2}}} \left[ \exp\left(-\frac{(t-t_0+t_\delta)^2}{2\sigma^2}\right) - \exp\left(-\frac{(t-t_0-t_\delta)^2}{2\sigma^2}\right) \right]$$

or

-continued $$g_{t_0,t_\delta,\omega}(t) =$$

$$\frac{1}{\sqrt{2(1-e^{-1/\omega^2})}\sqrt{\pi\omega^2 t_\delta^2}}\left[\exp\left(-\frac{(t-t_0+t_\delta)^2}{2\omega^2 t_\delta^2}\right) - \exp\left(-\frac{(t-t_0-t_\delta)^2}{2\omega^2 t_\delta^2}\right)\right]$$

In the following, the dependencies of $g_{t0,t\delta,\omega}$ will be implied, and the notation becomes simply g. Also, the parameters $\omega$ and $\sigma$ will be alternately used. This is done for relatively arbitrary notation reasons. The projection (or inner product, or convolution or correlation or component) of the template function on the measured data f(t) is given by $$C(t_0,t_\delta,\omega)=\int f(t)g(t)dt$$

It is clear that $\int g\, dt=0$. For the second moment (or $L^2$ norm) can be found:

$$\int g^2 dt = \frac{1}{2(1-e^{-t_\delta^2/\sigma^2})\sqrt{\pi\sigma^2}}\int\left[\exp\left(-\frac{2(t-t_0+t_\delta)^2}{2\sigma^2}\right)\right]dt + \quad (1)$$

$$\frac{1}{2(1-e^{-t_\delta^2/\sigma^2})\sqrt{\pi\sigma^2}}\int\left[\exp\left(-\frac{2(t-t_0+t_\delta)^2}{2\sigma^2}\right)\right]dt - \quad (2)$$

$$\frac{1}{2(1-e^{-t_\delta^2/\sigma^2})\sqrt{\pi\sigma^2}}\int\left[\exp\left(-\frac{(t-t_0+t_\delta)^2}{2\sigma^2}\right)\right. \quad (3)$$

$$\left.\exp\left(-\frac{(t-t_0-t_\delta)^2}{2\sigma^2}\right)\right]dt$$

$$= \frac{1}{2(1-e^{-t_\delta^2/\sigma^2})}\left\{1 - \frac{1}{\sqrt{\pi\sigma^2}}\int\left[\exp\left(-\frac{(t+t_\delta)^2+(t-t_\delta)^2}{2\sigma^2}\right)\right]dt\right\} \quad (4)$$

$$= \frac{1}{(1-e^{-t_\delta^2/\sigma^2})}\left\{1 - \frac{1}{\sqrt{\pi\sigma^2}}\int\left[\exp\left(-\frac{t^2+t_\delta^2}{\sigma^2}\right)\right]dt\right\} \quad (5)$$

$$= \frac{1}{(1-e^{-t_\delta^2/\sigma^2})}\left\{1 - \frac{\exp(-t_\delta^2/\sigma^2)}{\sqrt{\pi\sigma^2}}\int\left[\exp\left(-\frac{t^2}{\sigma^2}\right)\right]dt\right\} \quad (6)$$

$$= \frac{1}{(1-e^{-t_\delta^2/\sigma^2})}\left\{1-e^{-t_\delta^2/\sigma^2}\right\} \quad (7)$$

$$= 1 \quad (8)$$

The $L^2$ norm is thus independent of $t_0$, $t_\delta$, $\omega$.

The least squares problem of finding the best template function to fit the data is defined as:

$$\min_{t_0,t_\delta,w,\alpha}\int(f-\alpha g)^2 dt \quad (9)$$

in which $\alpha$ is an amplitude scaling factor. Multiplying this out gives $$\min_{t_0,t_\delta,w,\alpha}\left[\int f^2 dt + \alpha^2\int g^2 dt - 2\alpha\int fg\, dt\right]$$

The first two terms are independent of $t_0$, $t_\delta$, $\omega$ and finding the minimum of equation (9) with respect to just $t_0$, $t_\delta$, $\omega$ is equivalent to finding the maximum of the last dot product term. Writing $$C_m = \max_{t_0,t_\delta,w}\int fg\, dt,$$

For this maximum and $\|f\|^2=\int f^2$, a quadratic expression is obtained for the amplitude, given by $$\alpha^2 - 2C_m\alpha + \|f\|^2,$$

or $$(\alpha-C_m)^2 - C_m^2 + \|f\|^2.$$

The minimum of this parabola lies at $$\alpha=C_m. \quad (10)$$

Hence the methods of finding the minimum in the least squares in a 4D (4 parameter) search or finding the maximum in the correlation using a 3D (3 parameter) search and then calculating the amplitude from the correlation using Equation (10) are equivalent.

Figure 6:
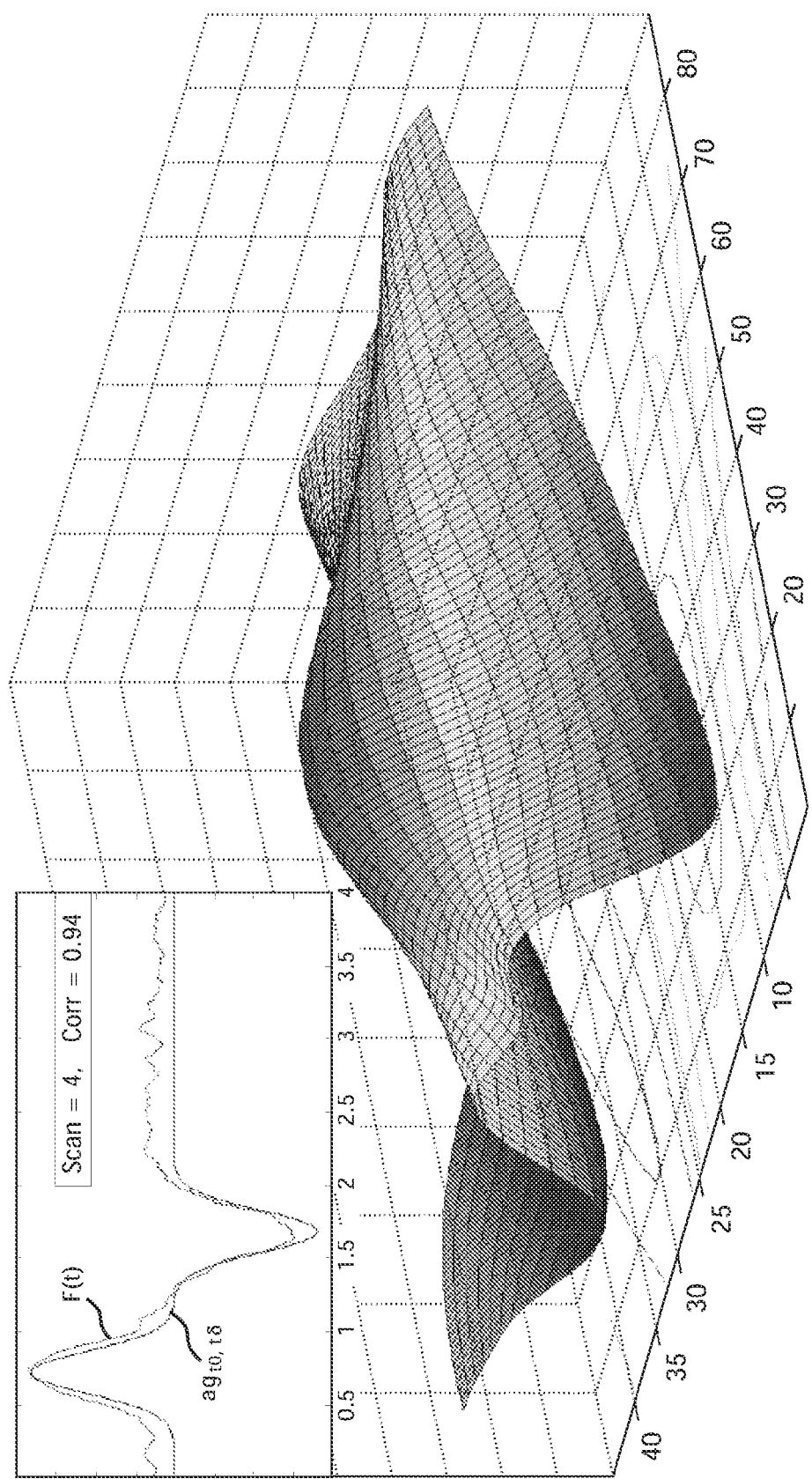
FIG. 6 is an illustration of the fit of an experimental trace.

FIG. 6 illustrates a typical trace of the in-phase component of the low frequency signal. The surface illustrates $\int f\, g$ for a range of $t_0$, $t_\delta$ values. The surface plot exhibits a clear maximum and this corresponds to values $t_0=1.2$ ms from the start of the trace and $2t_\delta=0.96$ ms. The width parameter used to calculate $\sigma=\omega t_\delta$, was set at $\omega=0.3$. The measured trace f(t) and the best fit a $g_{t0,t\delta}$ are illustrated at the inset. As can be seen, a good fit is obtained.

For sufficiently small $\omega$ the peak to peak value is given by $$S_{pp} = \frac{2\alpha}{\sqrt{2(1-e^{-1/\omega^2})}\sqrt{\pi\sigma^2}}.$$

In the above, the correlation has been used as proxy for the least squares fit. The correlation coefficient provides a measure for the quality of that fit. This number can be used to accept, or reject, a measurement or fit. In statistics, the correlation coefficient between two (stochastic) variables is given by $$\rho_{X,Y} = \frac{\text{cov}(X,Y)}{\sigma_X\sigma_Y} = \frac{E(X,Y)-E(X)E(Y)}{\sqrt{E(X^2)-E^2(X)}\sqrt{E(Y^2)-E^2(Y)}}$$

In the present case, the measurement f(t) and the least squares fit $ag_{t0,t\delta}(t)$ are interpreted as stochastic variables with $E(f)=E(g)=0$, and the following is obtained:

$$cc = \frac{\int fg\, dt}{\|f\|}$$

The methods described can be used to measure platelet events within a relatively noisy system, for example it can be used with measurements as described in Cheung et al., "Impedance spectroscopy flow cytometry: On-chip label-free cell differentiation", Cytometry Part A vol 65A, pp. 124-132, 2005.

Figure 7:
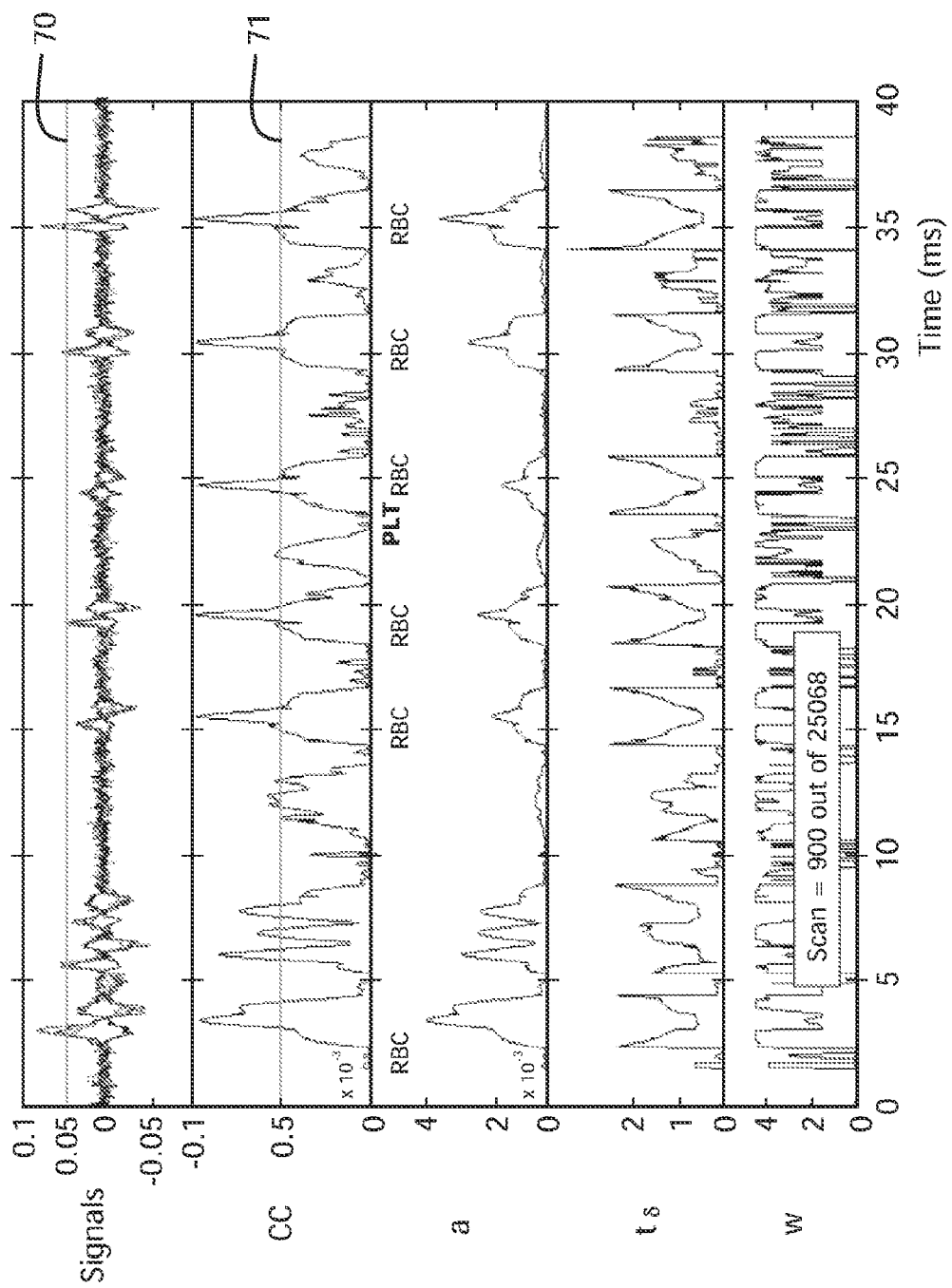
FIG. 7 illustrates measurement results of several RBC events and one accepted PLT event.

FIG. 7 illustrates the resulting traces in the top diagram. The line 70 illustrates the trigger level that is used in conventional event detection. The next diagram illustrates the maximum correlation coefficient (cc) level, on a scale from 0 to 1, that can be achieved by varying a, $t_\delta$, $\omega$ as a function of $t_0$. As can be seen, the cc trace shows peaks that most of the time correspond to clearly distinguishable (RBC) events in the top diagram. Some events (around 7 ms) can be interpreted as double, or even triple cell events. Of particular interest is the event around 22 ms. The correlation coefficient clearly peaks although no event can be seen in the top diagram. The amplitude trace in the third diagram also shows a peak and the ω and $t_\delta$ parameters in the fourth and fifth diagrams also show acceptable values. This event is interpreted as a platelet event.

Also worth noting are the events around 12 ms. Here the correlation coefficient does rise above the 50% trigger level 71, but the other parameters in the fourth and fifth diagram do not correspond to physical values, for instance the $t_\delta$ is too short for a real cell or particle to traverse the distance between the two sets of electrodes in the channel, or the ω is too small to correspond to a particle, however small, travelling over the finite size electrodes. Hence such events are attributed to noise, and rejected.

The trace in FIG. 7 is representative of 1000s of traces in a typical experiment.

While the invention has been illustrated and described in detail in the drawings and foregoing description, such illustration and description are to be considered illustrative or exemplary and not restrictive. The invention is not limited to the disclosed embodiments, but is only limited by the appended independent claims.

For example, it is possible to operate the invention in an embodiment wherein more than two electrode pairs are provided. This embodiment comes at the expense of greater complexity in the sensing electronics.

Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage.

It should be noted that the use of particular terminology when describing certain features or aspects of the invention should not be taken to imply that the terminology is being re-defined herein to be restricted to include any specific characteristics of the features or aspects of the invention with which that terminology is associated.

The invention claimed is:

1. A measurement device for investigating particles which are suspended in a carrier liquid, comprising at least a first pair of measurement electrodes for carrying out an electrical measurement of the particles, wherein at least one electrode of the pair of measurement electrodes is a fingered electrode having a plurality of fingers, wherein the fingers are positioned perpendicular to a flow of the carrier liquid and wherein the fingers are irregularly spaced according to a random sequence code, wherein the irregular spacing provides an improved signal to noise ratio for the measurement device.

2. The measurement device according to claim 1, wherein both electrodes of an electrode pair are fingered electrodes.

3. The measurement device according to claim 1, wherein a pattern of the fingers corresponds to a pseudorandom number sequence.

4. The measurement device according to claim 1, furthermore comprising a second pair of measurement electrodes.

5. The measurement device according to claim 4, wherein the second pair of measurement electrodes has at least one fingered electrode, wherein the fingers of one electrode of the first pair of electrodes are interdigitated with the fingers of one electrode of the second pair of electrodes.

6. The measurement device according to claim 1, wherein at least one of the fingered electrodes has a plurality of fingers with a non periodic design.

7. The measurement device according to claim 1, wherein at least one fingered electrode structure has a variable electrode finger width and/or variable spacing width.

8. A microfluidic system comprising a measurement device according to claim 1.

9. A cell sorter comprising a microfluidic system according to claim 8.

10. A method for investigating particles suspended in a carrier liquid, the method comprising
carrying out an electrical measurement process on at least one particle using at least one measurement electrode pair of which at least one electrode is a fingered electrode having a plurality of fingers that are positioned perpendicular to a flow of the carrier liquid and wherein the fingers are irregularly spaced according to a random sequence code, wherein the irregular spacing provides an improved signal to noise ratio for performing the electrical measurement process, thus generating a measurement signal, and
determining from the measurement signal presence of a particle in the carrier liquid.

11. The method according to claim 10, wherein carrying out an electrical measurement process comprises impedance measuring.

12. The method according to claim 11, wherein carrying out an electrical measurement process comprises impedance spectroscopy.

13. The method according to claim 10, further comprising carrying out a reference measurement, and comparing a result of the reference measurement with the measurement signal.

14. The method according to claim 10, wherein determining from the measurement signal presence of a particle in the carrier liquid comprises correlating a model curve describing passage of a particle between the fingers of the at least one measurement electrode pair of which at least one electrode is a fingered electrode with a section of the measurement signal.

* * * * *